(12) United States Patent
Shankar Setty et al.

(10) Patent No.: US 10,945,730 B2
(45) Date of Patent: Mar. 16, 2021

(54) STAPLING DEVICE WITH SELECTIVELY ADVANCEABLE ALIGNMENT PIN

(71) Applicant: Covidien LP, Mansfield, MA (US)

(72) Inventors: Jeevan Maddur Shankar Setty, Karnataka (IN); Sridharan Varadhan, Hyderabad (IN)

(73) Assignee: Covidien LP, Mansfield, MA (US)

( * ) Notice: Subject to any disclaimer, the term of this patent is extended or adjusted under 35 U.S.C. 154(b) by 400 days.

(21) Appl. No.: 16/016,759

(22) Filed: Jun. 25, 2018

(65) Prior Publication Data

US 2019/0388090 A1    Dec. 26, 2019

(51) Int. Cl.
*A61B 17/072* (2006.01)
*A61B 17/00* (2006.01)

(52) U.S. Cl.
CPC ........... *A61B 17/07207* (2013.01); *A61B 2017/00367* (2013.01); *A61B 2017/07271* (2013.01)

(58) Field of Classification Search
CPC .......... A61B 17/072; A61B 2017/0038; A61B 2017/00367; A61B 2017/2925
See application file for complete search history.

(56) References Cited

U.S. PATENT DOCUMENTS

| | | | |
|---|---|---|---|
| 1,158,111 A | 10/1915 | Khlheim | |
| 2,891,250 A | 6/1959 | Hirata | |
| 3,080,564 A | 3/1963 | Strekopitov et al. | |
| 3,252,643 A | 5/1966 | Strekopov et al. | |
| 3,269,630 A | 8/1966 | Fleischer | |
| 3,275,211 A | 9/1966 | Hirsch et al. | |
| 3,315,863 A | 4/1967 | O'Dea | |
| 3,494,533 A | 2/1970 | Green et al. | |
| 3,589,589 A | 6/1971 | Akopov | |
| 3,692,224 A | 9/1972 | Astafiev et al. | |
| 3,795,034 A | 3/1974 | Strekopytov et al. | |
| 3,822,818 A | 7/1974 | Strekopytov et al. | |
| 3,935,981 A | 2/1976 | Akopov et al. | |
| 3,949,923 A | 4/1976 | Akopov et al. | |
| 4,047,654 A | 9/1977 | Alvarado | |
| 4,216,891 A | 8/1980 | Behlke | |
| 4,244,372 A | 1/1981 | Kapitanov et al. | |

(Continued)

FOREIGN PATENT DOCUMENTS

EP    0136950 A2    4/1985

OTHER PUBLICATIONS

European Search Report dated Sep. 9, 2019, issued in EP Appln. No. 19182059.

*Primary Examiner* — Andrew M Tecco
(74) *Attorney, Agent, or Firm* — Carter, DeLuca & Farrell LLP

(57) ABSTRACT

A surgical stapling device includes an alignment pin pusher, an approximation assembly, and a linkage assembly. The linkage assembly includes a bell crank assembly including a bell crank and a bell crank pin. The bell crank pin is movable from an activated position to a deactivated position. In the activated position, the bell crank pin couples the alignment pin pusher to the approximation mechanism such that movement of the approximation mechanism causes movement of the alignment pin pusher from a retracted position to an advanced position. In the deactivated position, the bell crank pin is moved to a position to uncouple alignment pin assembly from the approximation mechanism.

18 Claims, 12 Drawing Sheets

(56) References Cited

U.S. PATENT DOCUMENTS

| | | |
|---|---|---|
| 4,296,881 A | 10/1981 | Lee |
| 4,305,539 A | 12/1981 | Korolkov et al. |
| 4,354,628 A | 10/1982 | Green |
| 4,378,901 A | 4/1983 | Akopov et al. |
| 4,383,634 A | 5/1983 | Green |
| 4,402,444 A | 9/1983 | Green |
| 4,415,112 A | 11/1983 | Green |
| D273,513 S | 4/1984 | Spreckelmeier |
| 4,442,964 A | 4/1984 | Becht |
| 4,470,533 A | 9/1984 | Schuler |
| 4,475,679 A | 10/1984 | Fleury, Jr. |
| 4,485,811 A | 12/1984 | Chernousov et al. |
| 4,506,670 A | 3/1985 | Crossley |
| 4,506,671 A | 3/1985 | Green |
| 4,508,253 A | 4/1985 | Green |
| 4,522,327 A | 6/1985 | Korthoff et al. |
| 4,527,724 A | 7/1985 | Chow et al. |
| 4,530,453 A | 7/1985 | Green |
| 4,550,870 A | 11/1985 | Krumme et al. |
| 4,566,620 A | 1/1986 | Green et al. |
| 4,568,009 A | 2/1986 | Green |
| 4,573,622 A | 3/1986 | Green et al. |
| 4,580,712 A | 4/1986 | Green |
| 4,585,153 A | 4/1986 | Failla et al. |
| 4,589,582 A | 5/1986 | Bilotti |
| 4,602,634 A | 7/1986 | Barkley |
| 4,605,001 A | 8/1986 | Rothfuss et al. |
| 4,605,004 A | 8/1986 | Di Giovanni et al. |
| 4,606,344 A | 8/1986 | Di Giovanni |
| 4,606,345 A | 8/1986 | Dorband et al. |
| 4,607,636 A | 8/1986 | Kula et al. |
| 4,612,933 A | 9/1986 | Brinkerhoff et al. |
| 4,617,928 A | 10/1986 | Alfranca |
| 4,632,290 A | 12/1986 | Green et al. |
| 4,665,916 A | 5/1987 | Green |
| 4,684,051 A | 8/1987 | Akopov et al. |
| 4,714,187 A | 12/1987 | Green |
| 4,715,520 A | 12/1987 | Roehr, Jr. et al. |
| 4,728,020 A | 3/1988 | Green et al. |
| 4,767,044 A | 8/1988 | Green |
| 4,788,978 A | 12/1988 | Strekopytov et al. |
| 4,802,614 A | 2/1989 | Green et al. |
| 4,805,823 A | 2/1989 | Rothfuss |
| 4,819,853 A | 4/1989 | Green |
| 4,848,637 A | 7/1989 | Pruitt |
| 4,869,414 A | 9/1989 | Green et al. |
| 4,881,544 A | 11/1989 | Green et al. |
| 4,881,545 A | 11/1989 | Isaacs et al. |
| 4,915,100 A | 4/1990 | Green |
| 4,930,503 A | 6/1990 | Pruitt |
| 4,938,408 A | 7/1990 | Bedi et al. |
| 4,941,623 A | 7/1990 | Pruitt |
| 4,951,861 A | 8/1990 | Schulze et al. |
| 4,964,559 A | 10/1990 | Deniega et al. |
| 5,005,754 A | 4/1991 | Van Overloop |
| 5,018,657 A | 5/1991 | Pedlick et al. |
| 5,071,052 A | 12/1991 | Rodak et al. |
| 5,100,042 A | 3/1992 | Gravener et al. |
| 5,116,349 A | 5/1992 | Aranyi |
| 5,137,198 A | 8/1992 | Nobis et al. |
| 5,172,845 A | 12/1992 | Tejeiro |
| 5,190,203 A | 3/1993 | Rodak |
| 5,219,111 A | 6/1993 | Bilotti et al. |
| 5,240,163 A | 8/1993 | Stein et al. |
| 5,344,060 A | 9/1994 | Gravener et al. |
| 5,368,599 A | 11/1994 | Hirsch et al. |
| 5,405,073 A | 4/1995 | Porter |
| 5,413,267 A | 5/1995 | Solyntjes et al. |
| 5,439,155 A | 8/1995 | Viola |
| 5,452,836 A | 9/1995 | Huitema et al. |
| 5,458,279 A | 10/1995 | Plyley |
| 5,462,215 A | 10/1995 | Viola et al. |
| 5,464,144 A | 11/1995 | Guy et al. |
| 5,465,894 A | 11/1995 | Clark et al. |
| 5,470,006 A | 11/1995 | Rodak |
| 5,470,008 A | 11/1995 | Rodak |
| 5,470,009 A | 11/1995 | Rodak |
| 5,497,934 A | 3/1996 | Brady et al. |
| 5,503,320 A | 4/1996 | Webster et al. |
| 5,509,596 A | 4/1996 | Green et al. |
| 5,542,594 A | 8/1996 | McKean et al. |
| 5,547,117 A | 8/1996 | Hamblin et al. |
| 5,558,266 A | 9/1996 | Green et al. |
| 5,579,978 A | 12/1996 | Green et al. |
| 5,580,067 A | 12/1996 | Hamblin et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,615,820 A | 4/1997 | Viola |
| 5,641,111 A | 6/1997 | Ahrens et al. |
| 5,678,748 A | 10/1997 | Plyley et al. |
| 5,697,543 A | 12/1997 | Burdorff |
| 5,706,997 A | 1/1998 | Green et al. |
| 5,706,998 A | 1/1998 | Plyley et al. |
| 5,732,871 A | 3/1998 | Clark et al. |
| 5,735,445 A | 4/1998 | Vidal et al. |
| 5,794,834 A | 8/1998 | Hamblin et al. |
| 5,810,240 A | 9/1998 | Robertson |
| 5,855,311 A | 1/1999 | Hamblin et al. |
| 5,878,937 A | 3/1999 | Green et al. |
| 5,893,506 A | 4/1999 | Powell |
| 5,894,979 A | 4/1999 | Powell |
| 5,964,394 A | 10/1999 | Robertson |
| 6,045,560 A | 4/2000 | McKean et al. |
| 6,638,285 B2 | 10/2003 | Gabbay |
| 6,805,273 B2 | 10/2004 | Bilotti et al. |
| 6,817,508 B1 * | 11/2004 | Racenet ............... A61B 17/072 227/175.2 |
| 6,988,650 B2 * | 1/2006 | Schwemberger .... A61B 17/072 227/176.1 |
| 7,070,083 B2 | 7/2006 | Jankowski |
| 7,134,587 B2 | 11/2006 | Schwemberger et al. |
| 7,147,139 B2 | 12/2006 | Schwemberger et al. |
| 7,147,140 B2 | 12/2006 | Wukusick et al. |
| 7,204,404 B2 | 4/2007 | Nguyen et al. |
| 7,207,472 B2 * | 4/2007 | Wukusick ............ A61B 17/072 227/176.1 |
| 7,210,609 B2 | 5/2007 | Leiboff et al. |
| 7,237,708 B1 | 7/2007 | Guy et al. |
| 7,275,674 B2 * | 10/2007 | Racenet ............... A61B 17/072 227/175.1 |
| RE40,237 E | 4/2008 | Bilotti et al. |
| 7,407,076 B2 | 8/2008 | Racenet et al. |
| 7,431,190 B2 | 10/2008 | Hoffman |
| 7,522,854 B2 | 4/2009 | Kinouchi et al. |
| 7,549,563 B2 | 6/2009 | Mather et al. |
| 7,568,605 B2 | 8/2009 | Kruszynski |
| 7,641,092 B2 | 1/2010 | Kruszynski et al. |
| 7,717,312 B2 | 5/2010 | Beetel |
| 7,731,073 B2 | 6/2010 | Wixey et al. |
| 7,735,704 B2 | 6/2010 | Bilotti |
| 7,766,207 B2 | 8/2010 | Mather et al. |
| 7,810,690 B2 | 10/2010 | Bilotti et al. |
| 7,886,953 B2 | 2/2011 | Schwemberger et al. |
| 8,016,176 B2 | 9/2011 | Kasvikis et al. |
| 8,029,520 B2 | 10/2011 | Korvick et al. |
| 8,033,439 B2 * | 10/2011 | Racenet ............... A61B 17/072 227/176.1 |
| 8,070,038 B2 | 12/2011 | Kostrzewski |
| 8,231,041 B2 | 7/2012 | Marczyk et al. |
| 8,292,904 B2 | 10/2012 | Popovic et al. |
| 8,353,436 B2 | 1/2013 | Kasvikis |
| 8,360,296 B2 | 1/2013 | Zingman |
| 8,424,738 B2 | 4/2013 | Kasvikis |
| 8,499,994 B2 | 8/2013 | D'Arcangelo |
| 8,596,515 B2 | 12/2013 | Okoniewski |
| 8,627,994 B2 | 1/2014 | Zemlok et al. |
| 8,646,673 B2 | 2/2014 | Bilotti et al. |
| 8,757,467 B2 | 6/2014 | Racenet et al. |
| 8,955,732 B2 | 2/2015 | Zemlok et al. |
| 8,967,446 B2 | 3/2015 | Beardsley et al. |
| 9,022,273 B1 | 5/2015 | Marczyk et al. |
| 9,125,651 B2 | 9/2015 | Mandakolathur Vasudevan et al. |

(56) References Cited

U.S. PATENT DOCUMENTS

| | | |
|---|---|---|
| 9,192,382 B2 | 11/2015 | Kostrzewski |
| 2004/0164123 A1* | 8/2004 | Racenet ............... A61B 17/072 227/176.1 |
| 2005/0247752 A1 | 11/2005 | Kelly et al. |
| 2005/0247753 A1 | 11/2005 | Kelly et al. |
| 2006/0163312 A1 | 7/2006 | Viola et al. |
| 2007/0095877 A1* | 5/2007 | Racenet ............... A61B 17/072 227/175.2 |
| 2007/0187456 A1 | 8/2007 | Viola et al. |
| 2010/0048988 A1 | 2/2010 | Pastorelli et al. |
| 2013/0206813 A1 | 8/2013 | Nalagatla |
| 2016/0249914 A1 | 9/2016 | Zhang et al. |
| 2017/0014134 A1 | 1/2017 | Chen et al. |
| 2017/0027571 A1 | 2/2017 | Nalagatla et al. |
| 2017/0027572 A1 | 2/2017 | Nalagatla et al. |
| 2017/0027573 A1 | 2/2017 | Nalagatla et al. |
| 2017/0027574 A1 | 2/2017 | Nalagatla et al. |
| 2017/0238927 A1 | 8/2017 | Wan et al. |
| 2017/0340324 A1* | 11/2017 | Gong ................... A61B 17/072 |

\* cited by examiner

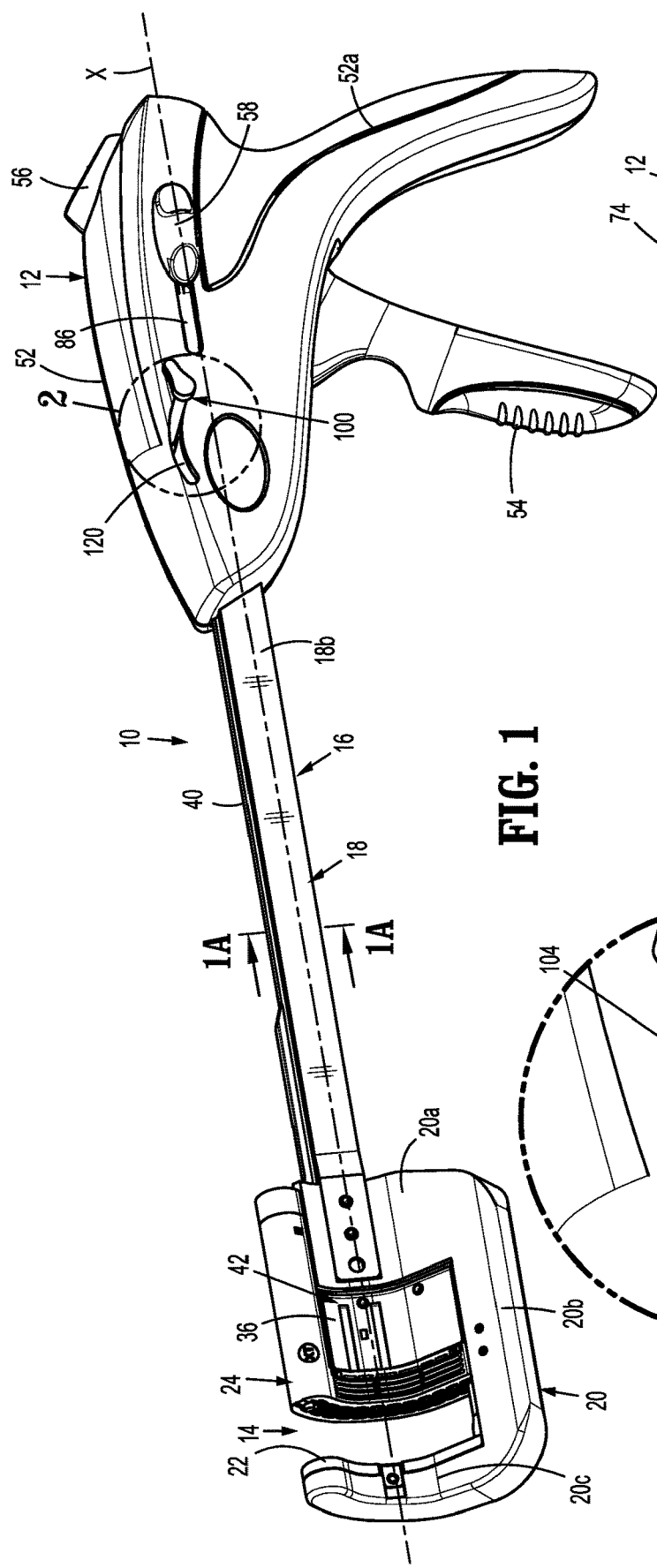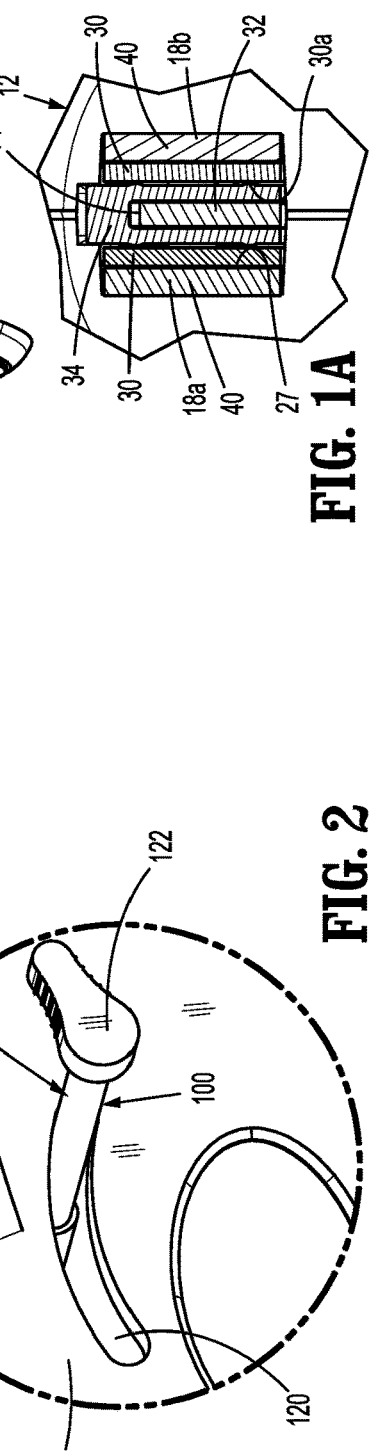

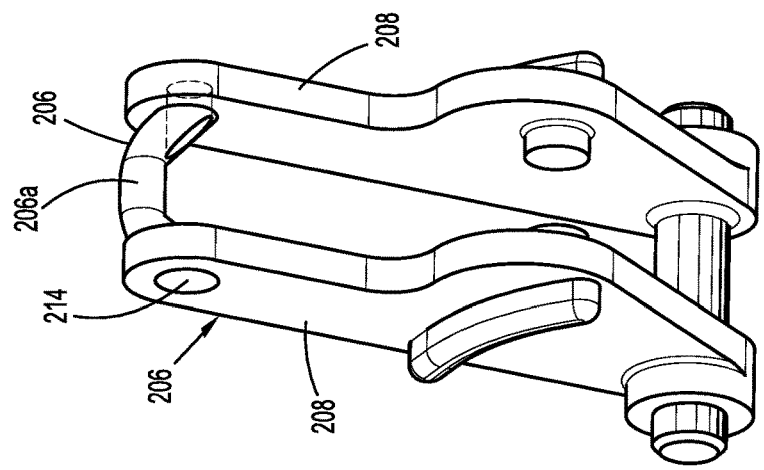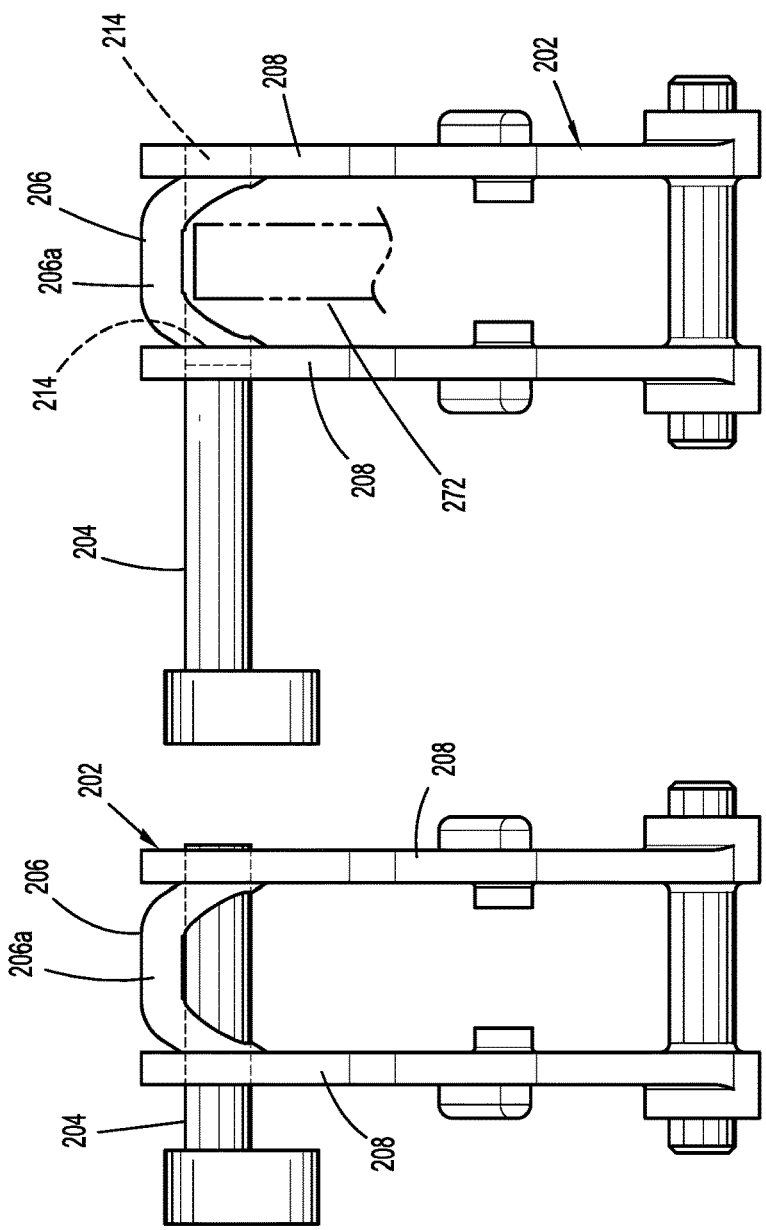

STAPLING DEVICE WITH SELECTIVELY ADVANCEABLE ALIGNMENT PIN

BACKGROUND

1. Technical Description

The present disclosure is directed to a surgical stapling device and, more particularly, to a surgical stapling device including an alignment pin assembly having an alignment pin that can be automatically or manually actuated or selectively deactivated.

2. Background of Related Art

Surgical stapling devices are used to apply parallel rows of staples through compressed living tissue to close tissue or organs prior to transection and resection procedures, or in anastomoses procedures. Such stapling devices include an anvil assembly, a cartridge assembly for supporting an array of surgical staples, an approximation mechanism for approximating the anvil and cartridge assemblies, an alignment pin assembly for capturing tissue between the cartridge and anvil assemblies and for maintaining alignment between the cartridge and anvil assemblies during approximation and firing, and a firing mechanism for ejecting the surgical staples from the cartridge assembly. Typically, the alignment pin assembly can be manually actuated to advance an alignment pin from the cartridge assembly into engagement with the anvil assembly or, alternatively, automatically actuated upon operation of the approximation mechanism of the stapling device.

In some stapling devices, the alignment pin assembly can be manually advanced or automatically advanced. In such stapling devices, if the alignment pin assembly is not manually advanced, the alignment pin assembly will be automatically advanced upon approximation of the stapling device. Thus, the alignment pin assembly is always moved to the advanced position to capture tissue between the anvil and cartridge assemblies prior to firing of the stapling device.

During some stapling procedures, the tissue or organ is too thick or wide to staple in a single actuation of the stapling device. Thus, two or more actuations of the stapling device are required to close the tissue or organ. In such situations, it may be desirable to allow the tissue to extend from between the anvil and cartridge assemblies, i.e., it may not be desirable to capture tissue between the anvil and cartridge assemblies with the alignment pin.

A continuing need exists in the art for a stapling device in which the alignment pin assembly can be selectively deactivated by a clinician when desired.

SUMMARY

One aspect of the disclosure is directed a stapling device including a handle assembly, a frame, a tool assembly, an alignment pin assembly, an approximation assembly, and a linkage assembly. The handle assembly includes a housing defining a stationary handle and a trigger pivotably supported on the housing. The frame extends distally from the housing. The tool assembly is supported on the distal portion of the frame and includes an anvil and a cartridge assembly. The cartridge assembly includes an alignment pin and is movable along the frame assembly between an open position and clamped position. The alignment pin assembly includes an alignment pin pusher having an abutment positioned to engage the alignment pin. The alignment pin pusher is movable between a retracted position and an advanced position to move the alignment pin from a position located within the cartridge assembly to a position extending from the cartridge assembly. The approximation mechanism supports the cartridge assembly and is coupled to the handle assembly. The approximation assembly is movable from a retracted position to an advanced position in response to actuation of the handle assembly to move the cartridge assembly from the open position to the clamped position. The linkage assembly includes a member extending through the housing that is accessible to a clinician. The member is movable from an activated position to a deactivated position. In the activated position, the linkage assembly couples the alignment pin assembly to the approximation mechanism such that movement of the approximation mechanism causes movement of the alignment pin pusher. In the deactivated position, the linkage assembly uncouples the alignment pin assembly from the approximation mechanism.

In embodiments, the linkage assembly includes a bell crank assembly that having a bell crank and the member, wherein the member includes a bell crank pin.

In some embodiments, the bell crank pin is pivotably connected to the frame and, in the activated position is coupled to the approximation mechanism.

In certain embodiments, the approximation mechanism includes clamp slide members wherein the clamp slide members have distal head portions configured to receive the cartridge assembly.

In embodiments, the clamp slide members define a cam slot and the bell crank includes cam members that are received in the cam slots such that longitudinal movement of the clamp slide members causes pivotal movement of the bell crank.

In some embodiments, the alignment pin pusher includes a clip defining a recess, and the bell crank pin is positioned within the recess in the activated position to couple the bell crank to the alignment pin pusher such that rotation of the bell crank causes longitudinal movement of the alignment pin pusher.

In certain embodiments, the clip is formed of a resilient material.

In embodiments, the clip has a C-shaped configuration such that the bell crank pin can be removed from the recess of the clip when the alignment pin pusher is advanced manually independently of the clamp slide members.

In some embodiments, the alignment pin pusher includes radially extending posts that extend through first elongated slots in the housing of the handle assembly, and each of the posts support a knob, wherein the knobs are movable along the housing to manually advance the alignment pin pusher.

In certain embodiments, the cartridge assembly includes a body defining a slot and the alignment pin is received within the slot.

In embodiments, the abutment is movable within the slot in the body of the cartridge assembly to move the alignment pin from a retracted position located within the slot to an advanced position projecting from the slot.

In some embodiments, the alignment pin pusher includes an intermediate portion that supports the clip, and the intermediate portion defines a channel that accommodates the bell crank when the alignment pin is manually advanced independently of the clamp slide members.

In certain embodiments, the bell crank pin includes a grip member that is positioned adjacent an outer surface of the housing and is movable to move the bell crank pin between the activated and inactivated positions.

In embodiments, the bell crank defines at least one opening that receives the bell crank pin when the bell crank pin is in the activated position.

In some embodiments, the frame includes an elongate body portion that defines a longitudinal axis and a distal body portion that supports the tool assembly.

In certain embodiments, the distal body portion of the frame includes a proximal transverse portion, a linear portion, and a distal transverse portion, wherein the distal transverse portion supports the anvil.

In embodiments, the distal body portion is U-shaped.

In some embodiments, the stapling device includes a firing bar that is movable in response to actuation of the handle assembly to eject staples from the cartridge assembly.

In certain embodiments, the housing defines a curved slot and the bell crank pin extends through the curved slot as the bell crank pivots within the housing when the bell crank pin is in the activated position.

BRIEF DESCRIPTION OF THE DRAWINGS

Various embodiments of the presently disclosed stapling device are described herein below with reference to the drawings, wherein:

FIG. 1 is a side perspective view of an exemplary embodiment of the presently disclosed stapling device with a tool assembly in an open position;

FIG. 1A is a cross-sectional view taken along section line 1A-1A;

FIG. 2 is an enlarged view of the indicated area of detail shown in FIG. 1;

FIG. 6A is a top view of the alignment pin pusher of FIG. 6;

FIG. 15 is a view of an alternate embodiment of the bell crank assembly of the stapling device shown in FIG. 1 from the proximal end with the bell crank pin in an activated position;

FIG. 16 is a view of the bell crank assembly of FIG. 15 from the proximal end with the bell crank pin in a deactivated position; and FIG. 17 is a perspective view from the proximal end of the bell crank of the bell crank assembly shown in FIG. 16.

DETAILED DESCRIPTION OF EMBODIMENTS

Figure 3:
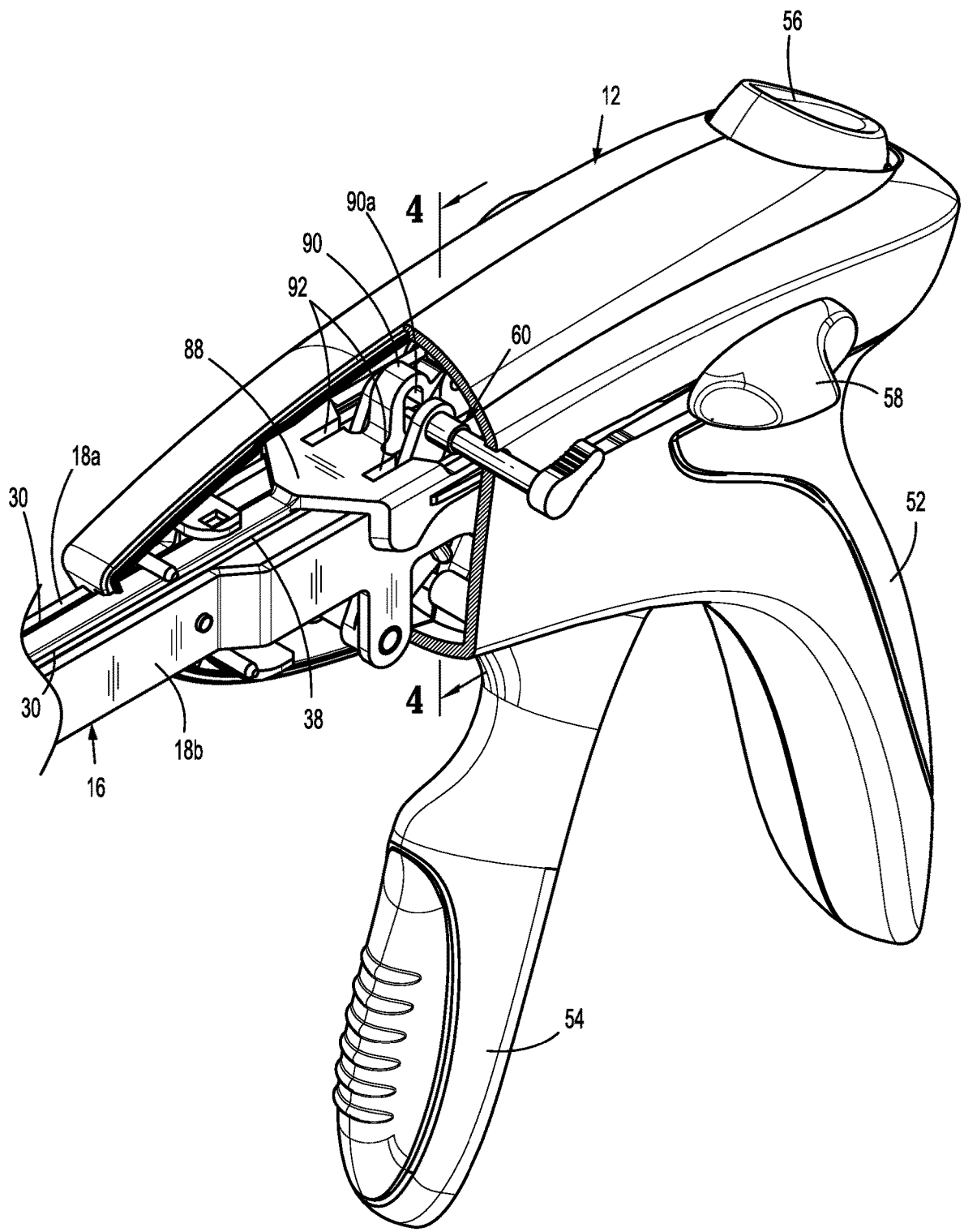
FIG. 3 is a side perspective view of a handle assembly of the stapling device shown in FIG. 1 with a portion of a housing section cutaway and a bell crank pin of a bell crank assembly of the handle assembly in a deactivated position.

The presently disclosed stapling device will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "clinician" is used generally to refer to medical personnel including doctors, nurses, and support personnel.

FIGS. 1-3 illustrate an exemplary embodiment of the presently disclosed surgical stapling device shown generally as stapling device 10. The stapling device 10 includes a handle assembly 12, a tool assembly 14, and a frame 16 that extends from the handle assembly 12 to the tool assembly 14. The frame 16 includes an elongate body portion 18 defining a longitudinal axis "X" and a distal body portion 20. The elongate body portion 18 includes laterally spaced elongated frame members 18a, 18b (FIG. 1A) that extend from the handle assembly 12 to the tool assembly 14 and support various components of the stapling device 10 as described below. The distal body portion 20 of the frame 16 is substantially C or U-shaped and includes a proximal transverse portion 20a, a linear portion 20b, and a distal transverse portion 20c. The proximal transverse portion 20a of the distal body portion 20 of the frame 16 is connected to a distal portion of the frame members 18a, 18b and is connected to the distal transverse portion 20c of the distal body portion 20 by the linear portion 20b of the distal body portion 20. The proximal transverse portion 20a and the distal transverse portion 20c define spaced axes that are substantially perpendicular to the longitudinal axis "X" of the elongate body portion 18.

Figure 13:
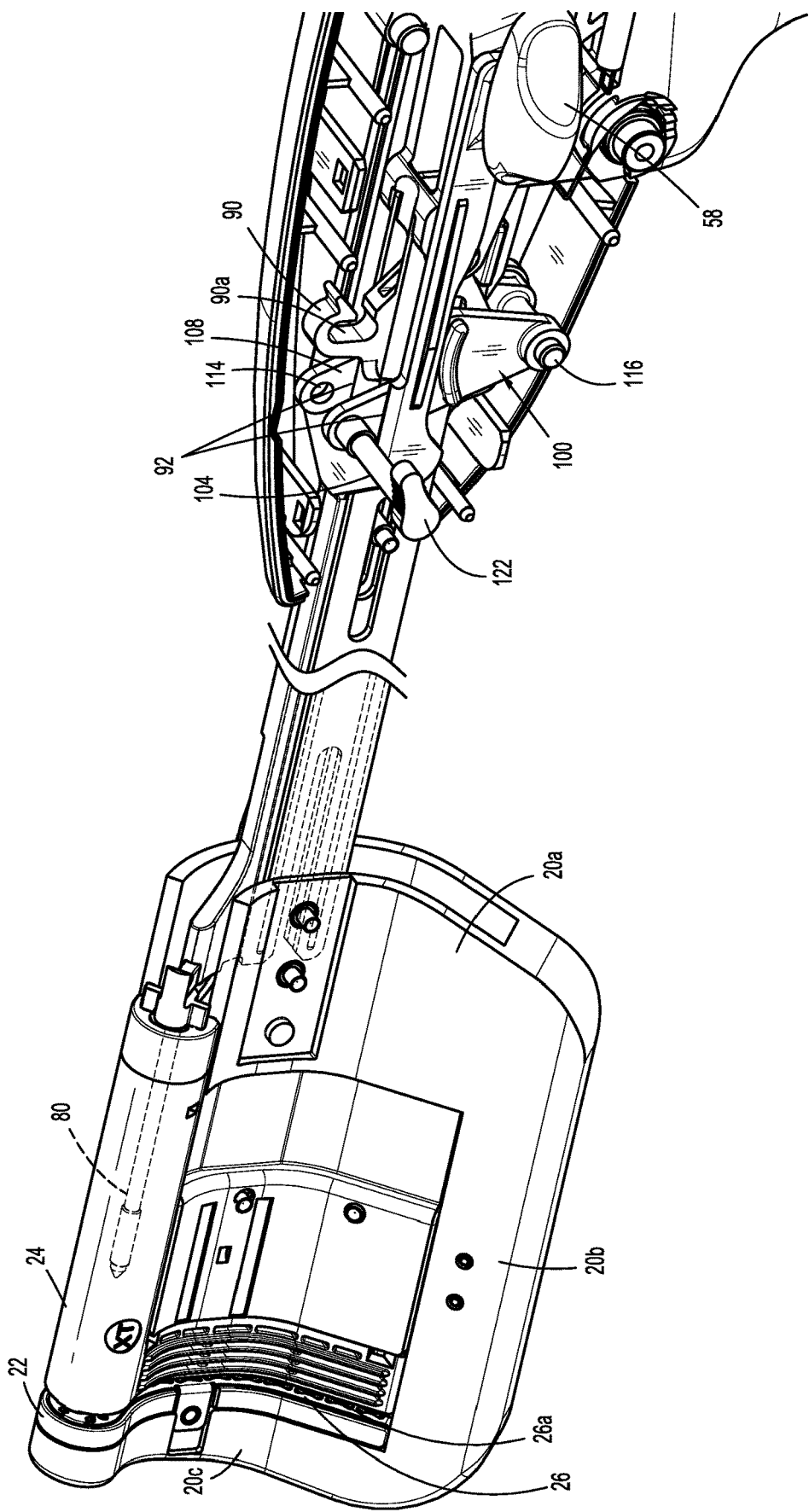
FIG. 13 is a side perspective partial cutaway view of the stapling device of FIG. 10 with the housing section of the handle assembly removed, the bell crank pin of the bell crank assembly in the deactivated position, the tool assembly in a clamped position, and the alignment pin assembly in a retracted position.

The tool assembly 14 includes an anvil 22 and a cartridge assembly 24. The anvil 22 is supported on the distal transverse portion 20c of the distal body portion 20 and includes an anvil surface 26 (FIG. 13) that defines a plurality of staple deforming pockets 26a (FIG. 13). The cartridge assembly 24 is supported for movement within the space 30 defined between the proximal and distal transverse portions 20a, 20c from an open position (FIG. 1) spaced from the anvil 22 to a distal position in juxtaposed alignment with the anvil 22. In embodiments, the proximal and distal transverse portions 20a, 20c of the distal body portion 20 of the frame assembly 16, and the anvil 22 and cartridge assembly 24 of the tool assembly 14, may be curved along axes transverse to the longitudinal axis "X" of the elongate body portion 18. Alternately, the proximal and distal transverse portions 20a, 20c of the distal frame portion 20, and the anvil 22 and cartridge assembly 24 of the tool assembly 14, may define axes that are parallel to an axis transverse to the longitudinal axis "X".

The frame members 18a, 18b of the elongate body portion 18 of the frame assembly 16 are spaced from each other to define a channel 27 (FIG. 1A) that extends from the handle assembly 12 to the tool assembly 14. The frame members 18a, 18b support a pair of clamp slide members 30, a firing bar 32, and an alignment pin pusher 34. Each of the clamp slide members 30, the firing bar 32, and the alignment pin pusher 34 are movable within the channel 26 of the frame assembly 26 in response to actuation of the handle assembly 12 to operate functions of the stapling device 10 as described in further detail below.

Figure 7:
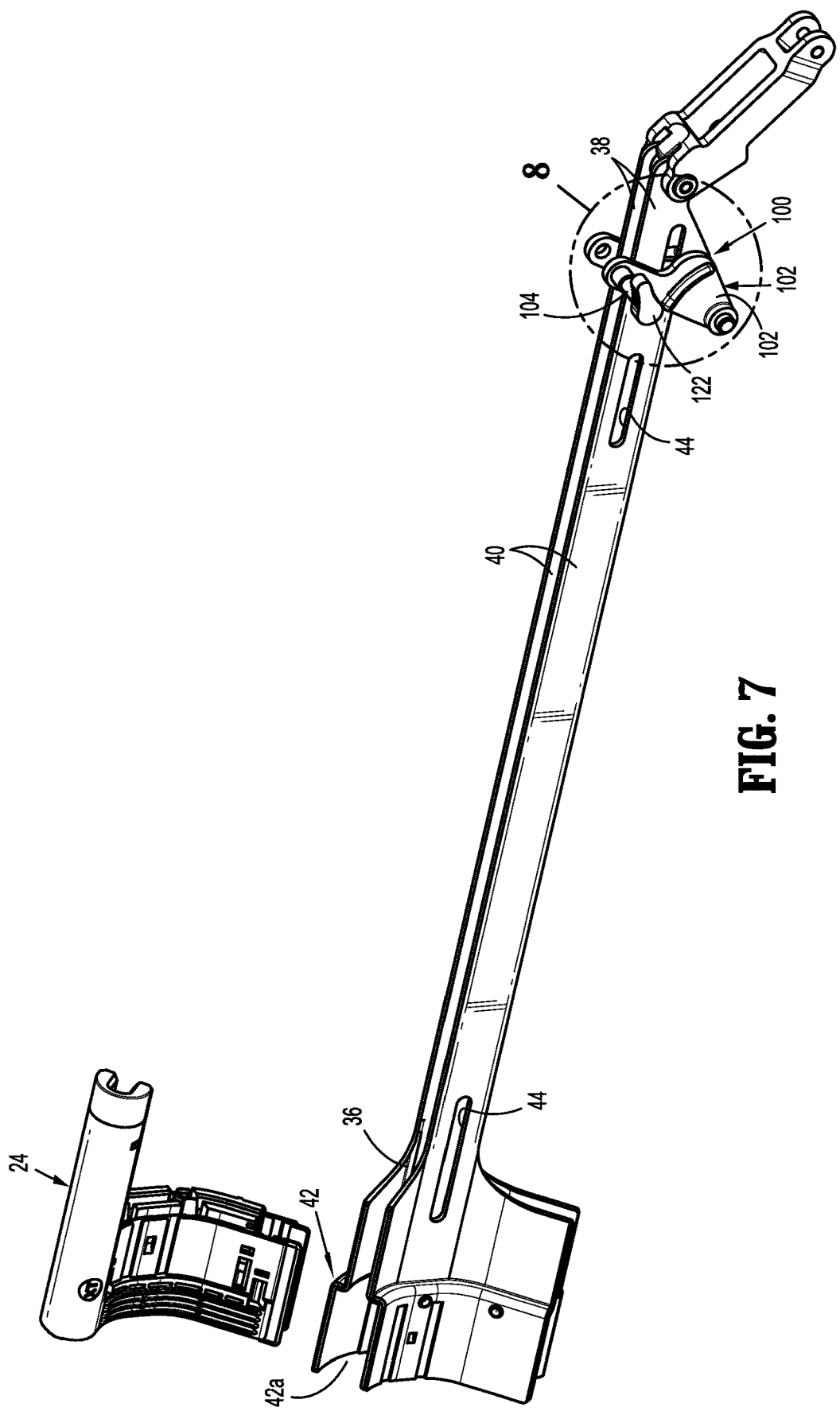
FIG. 7 is a side perspective view of a clamp slide assembly and a staple cartridge assembly of the stapling device shown in FIG. 1 with parts separated.
Figure 8:
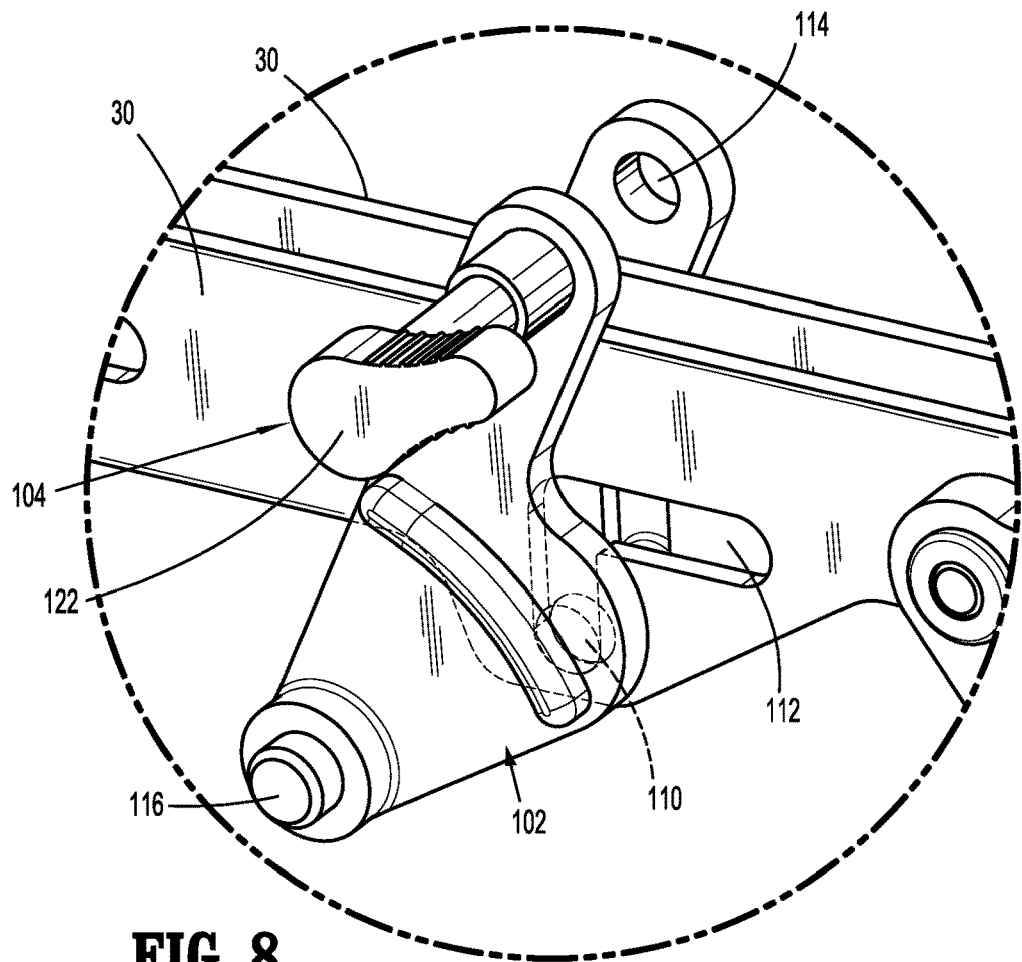
FIG. 8 is an enlarged view of the indicated area of detail shown in FIG. 7.

The clamp slide members 30 form part of an approximation mechanism of the stapling device 10. Each of the clamp slide members 30 has a distal portion 36 (FIG. 1), a proximal portion 38 (FIG. 3), and an elongate body 40 (FIG. 1A) that extends between the distal and proximal portions 36, 38, respectively, of the clamp slide members 30. The proximal portions 38 of the clamp slide members 30 are supported within the handle assembly 12. The elongate bodies 40 of the clamp slide members 30 are supported between the frame members 18a, 18b and are confined to linear movement by pins 44 (FIG. 11) that are positioned within slots 46 formed in the clamp slide members 30. The distal portion 36 of each of the clamp slide members 30 includes a head portion 42 (FIG. 7). The clamp slide members 30 are spaced from each other to define an elongated channel 30a (FIG. 1A) in which pin pusher 34 and firing bar 32 are positioned for movement between retracted and advanced positions. The head portion 42 of the clamp slide members 30 defines a cartridge support receptacle 42a (FIG. 7) for releasably supporting the cartridge assembly 24. The clamp slide members 30 are movable between the frame members 18a, 18b of the elongated body portion 18 of the frame assembly 16 to advance the cartridge assembly 24 from an open position (FIG. 1) spaced from the anvil 22 to a clamped position (FIG. 10) in juxtaposed alignment with the anvil 22. Similarly, the firing bar 32 is movable between retracted and advanced positions to eject staples from the cartridge assembly 24. For a more detailed description of the approximation and firing mechanisms of the presently disclosed stapling device 10, see U.S. Pat. No. 6,817,508 ("508 Patent") which is incorporated herein by reference in its entirety.

Figure 9:
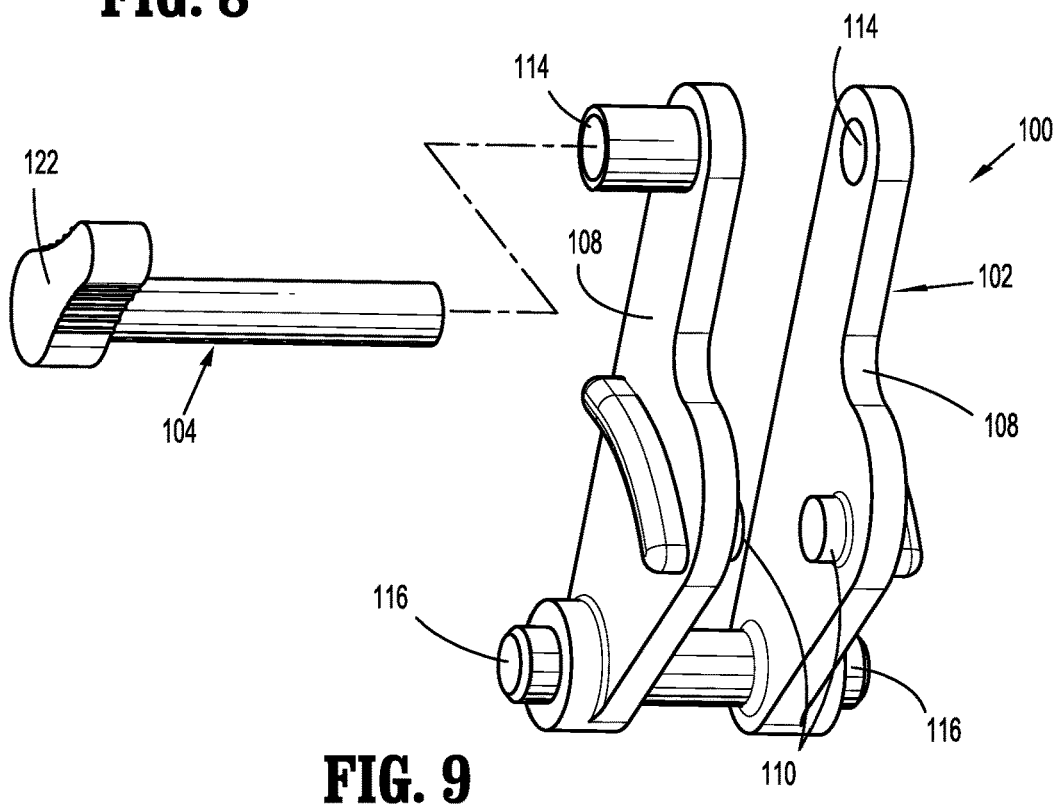
FIG. 9 is a perspective view from the proximal end of the bell crank assembly of the stapling device shown in FIG. 1 with the bell crank pin separated from a bell crank of the bell crank assembly.
Figure 10:
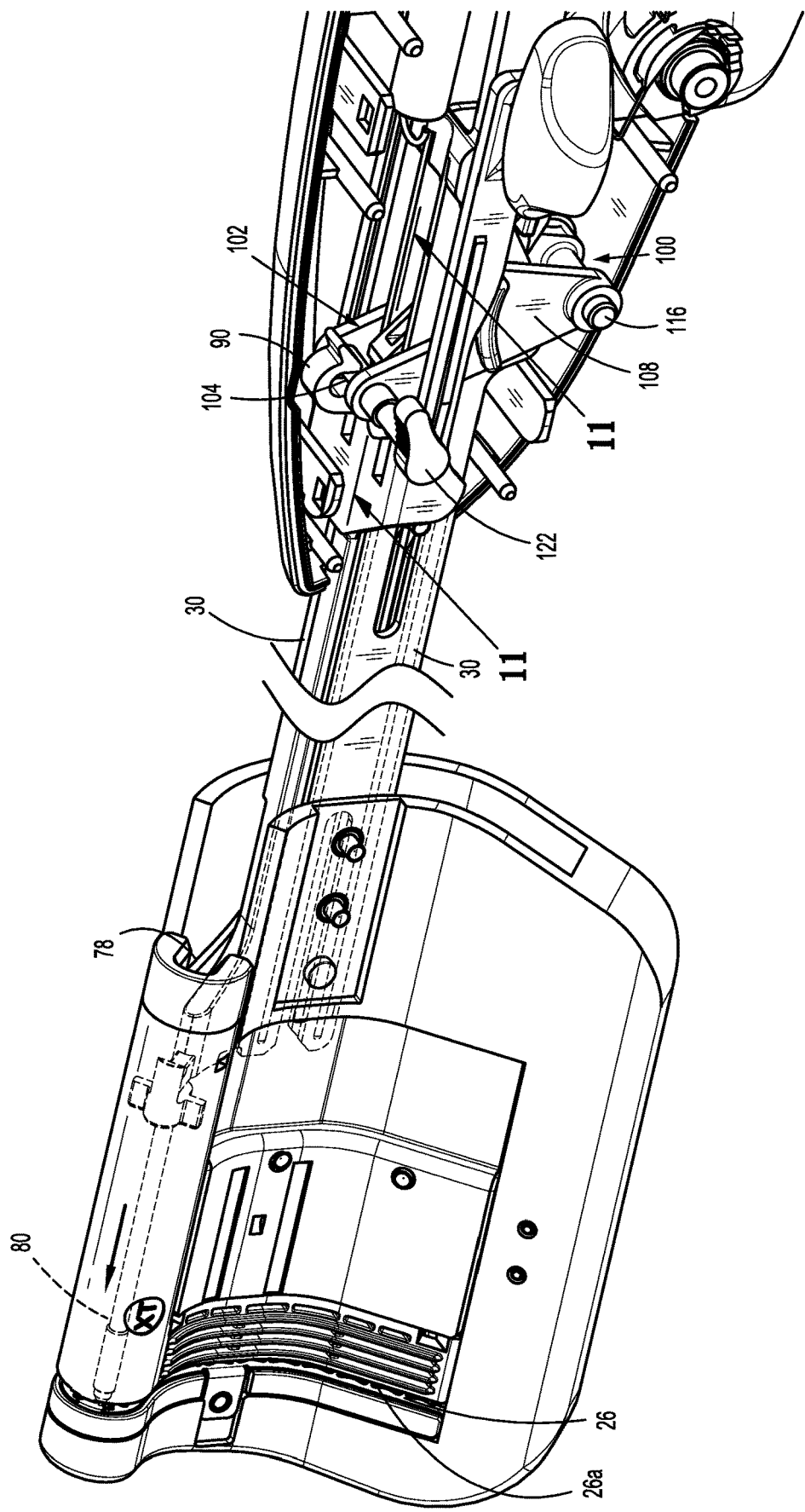
FIG. 10 is a side perspective partial cutaway view of the stapling device of FIG. 1 with a housing section of the handle assembly removed, the bell crank pin of the bell crank assembly in the activated position, the tool assembly in a clamped position, and the alignment pin assembly in an advanced position.
Figure 11:
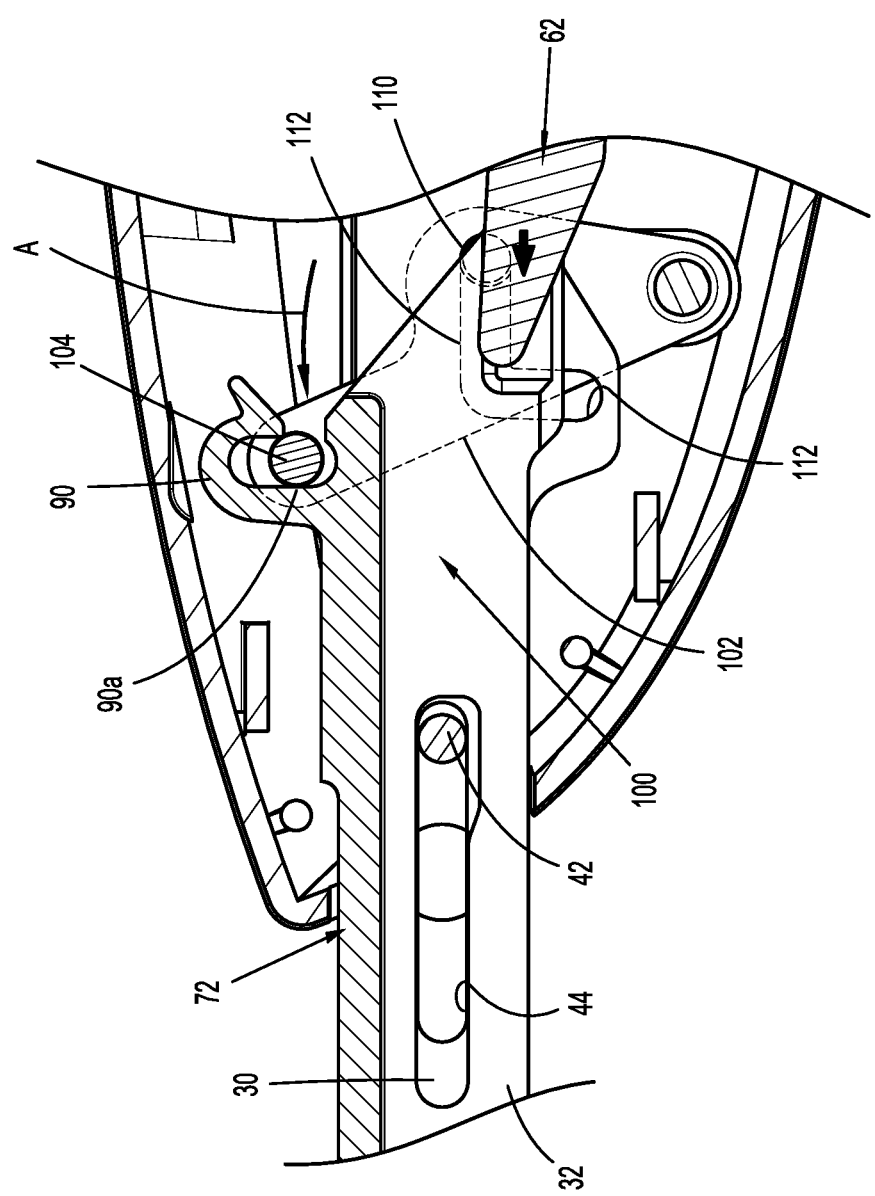
FIG. 11 is cross-sectional view taken along section lines 11-11 of FIG. 10.

The handle assembly 12 includes a housing 52 defining a stationary handle 52a, a pivotable trigger 54, a release button 56, knobs 58, and a bell crank assembly 100 (FIG. 9). In embodiments, the pivotable trigger 54 is positioned to engage a bi-linkage assembly (not shown) that is coupled to the proximal portion 38 (FIG. 3) of the clamp slide members 30 such that movement of the pivotable trigger 54 towards the stationary handle 52a causes the clamp slide members 30 to move from the retracted position to the advanced position to move the cartridge assembly 24 in relation to the anvil 22 from the open position (FIG. 1) to the clamped position (FIG. 10). The pivotable trigger 54 is also coupled to a firing link 62 (FIG. 11) that is positioned to engage a proximal end of the firing bar 32 when the clamp slide members 30 are in the advanced position and the firing bar 32 is in an intermediate position such that movement of the pivotable trigger 54 towards the stationary handle 52a causes the firing bar 32 to move through the cartridge assembly 24 to eject staples from the cartridge assembly 24 into the anvil 22. See, e.g., the '508 Patent for a more detailed description of the approximation and firing mechanisms of the stapling device 10.

Figure 4:
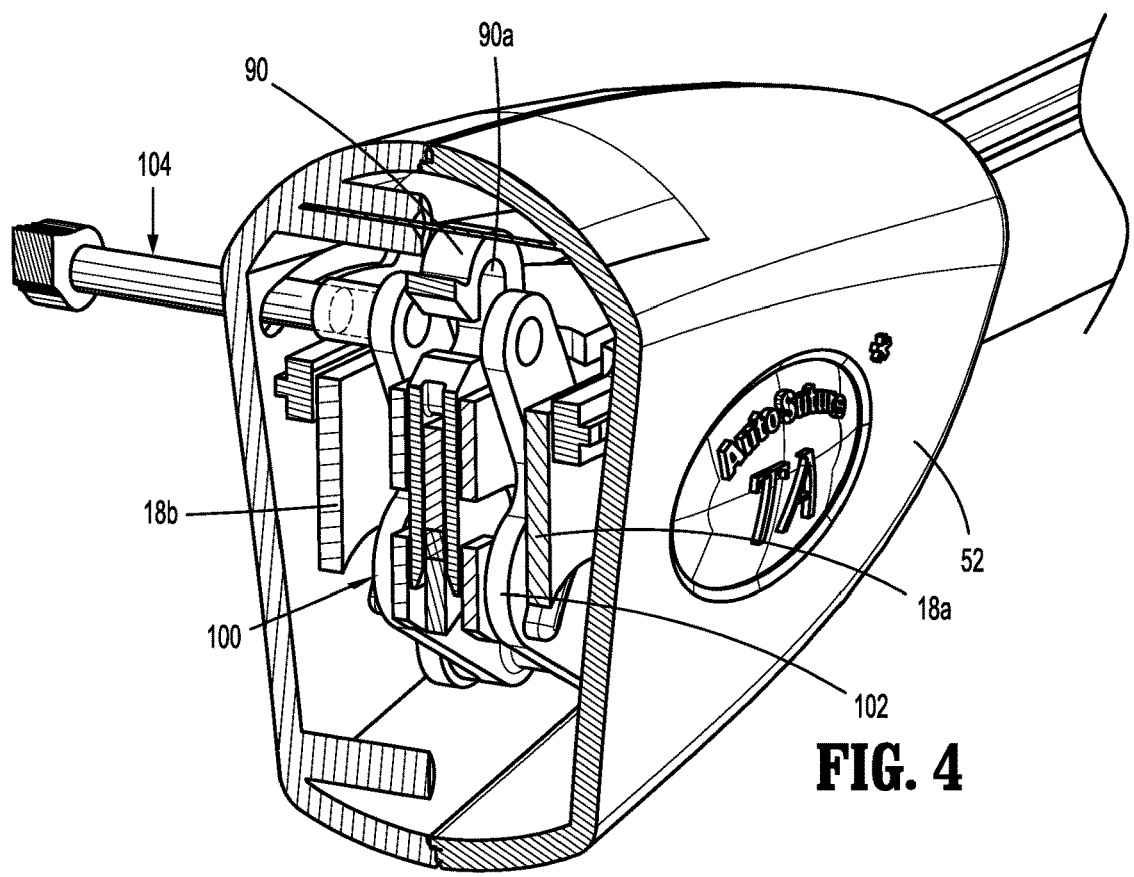
FIG. 4 is a cross-sectional view taken along section line 4-4 of FIG. 3.
Figure 5:
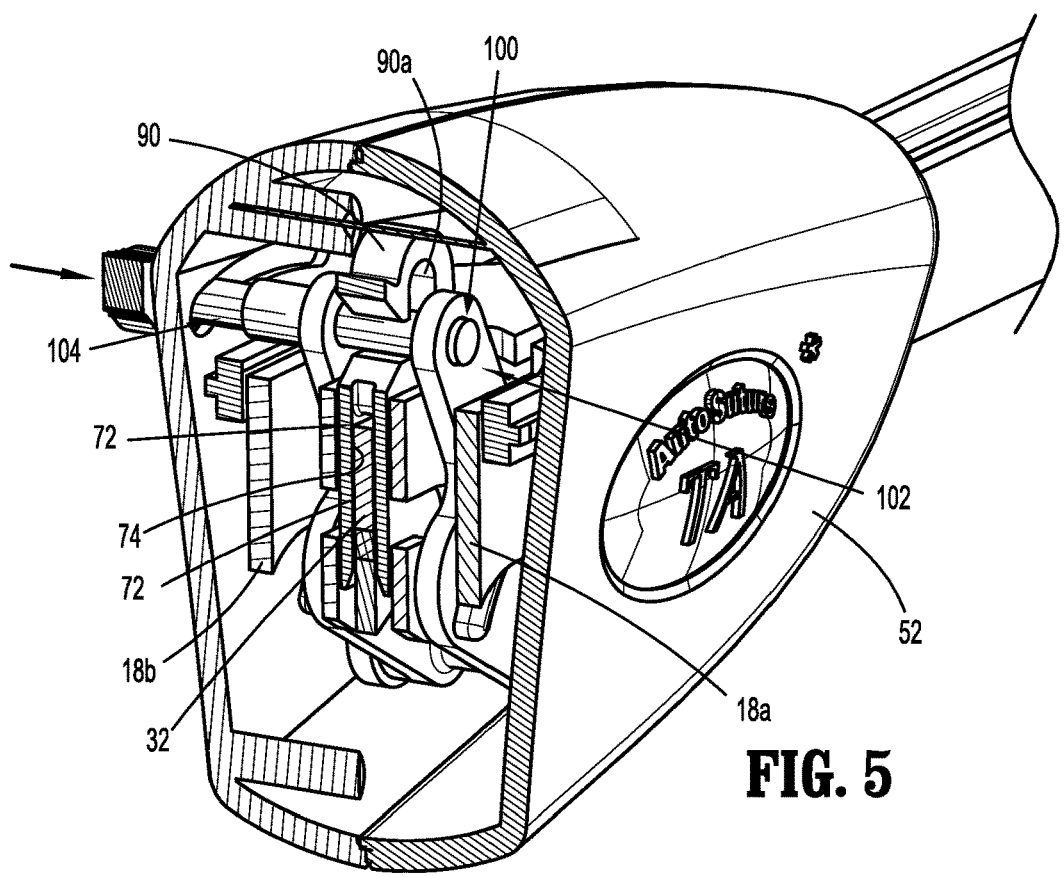
FIG. 5 is a cross-sectional view taken along section line 4-4 of FIG. 3 with the bell crank pin of the alignment pin assembly of the handle assembly in an activated position.
Figure 6:
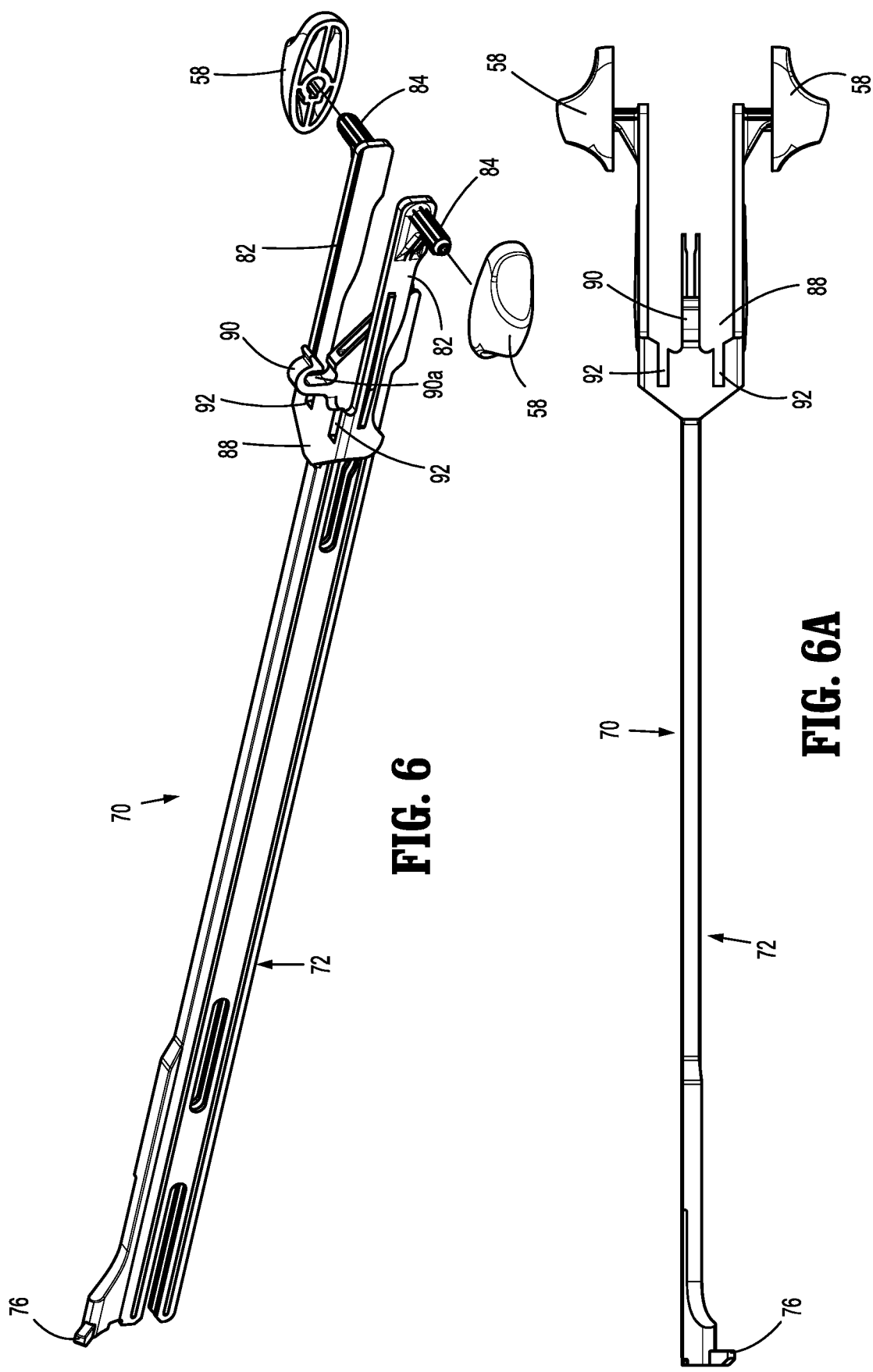
FIG. 6 is a side perspective view of the alignment pin pusher assembly of the stapling device shown in FIG. 1.

Referring to FIGS. 4-6, the stapling device 10 includes an alignment pin assembly 70 that includes an alignment pin pusher 72 and the knobs 58 of the handle assembly 12. The alignment pin pusher 72 includes a body 72a that defines a channel 74 (FIG. 5) along its length that receives the firing bar 32 such that the alignment pin pusher 72 is slidable independently of and in relation to the firing bar 32 between advanced and retracted positions. The alignment pin pusher 72 includes a distally positioned abutment member 76 that is positioned and dimensioned to be received within a slot 78 (FIG. 7) formed in the cartridge assembly 24. The slot 78 of the cartridge assembly 24 receives an alignment pin 80 (FIG. 10) that is positioned to be engaged by the abutment member 76 of the alignment pin pusher 72 such that movement of the alignment pin pusher 72 from a retracted position to an advanced position causes movement of the alignment pin 80 from a retracted position located within the slot 78 of the cartridge assembly 24 (FIG. 13) to an advanced position (FIG. 12) extending from a distal end of the cartridge assembly 24.

Figure 12:
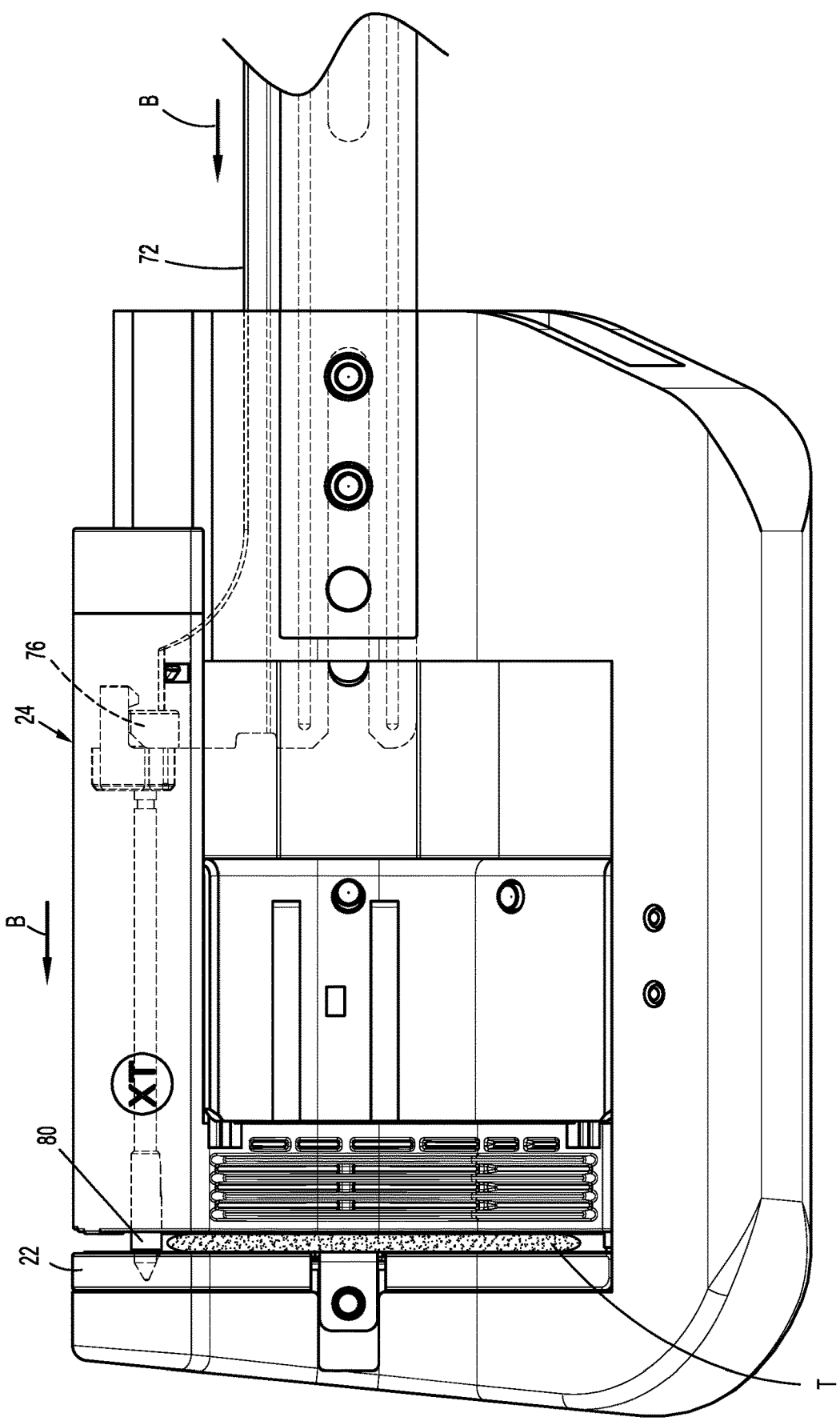
FIG. 12 is a side view of a distal portion of the stapling device of FIG. 10 with the tool assembly in the clamped position and the alignment pin assembly in the advanced position.

The alignment pin pusher 72 includes a pair of legs 82 that extend proximally from an intermediate portion 88 (FIG. 6) of the body 72a of the pin pusher 72 and support a radially extending post 84. Each of the radially extending posts 84 extends through a respective elongated slot 86 (FIG. 1) formed in the housing 52. The knobs 58 are supported on the posts 84 to be engaged by a thumb or other digit of a clinician to manually advance the alignment pin pusher 72 from the retracted position (FIG. 13) towards the advanced position (FIG. 12)

The intermediate portion 88 of the alignment pin pusher 72 supports a clip 90 having a substantially C-shape and defining a recess 90a. The clip 90 is formed from a resilient material that is flexible to facilitate attachment of the clip 90 to a bell crank assembly 100 as described in detail below. The intermediate portion 88 defines a pair of spaced slots 92 (FIG. 3).

Referring to FIGS. 6-9, the bell crank assembly 100 includes a bell crank 102 and a bell crank pin 104. The bell crank 102 includes spaced side walls 108 (FIG. 9) that include an inwardly extending cam member 110 that is configured to be received within cam slots 112 (FIG. 8) formed in the proximal portions 38 of the clamp slide members 30. Each of the side walls 108 also defines an opening 114 that is dimensioned to receive the bell crank pin 104. The bell crank pin 104 extends between the openings 114 in the side walls 108 of the bell crank 102 and is configured to be received within the recess 90a of the clip 90 of alignment pin pusher 72 to couple the bell crank 102 to the alignment pin pusher 72. The bell crank 102 includes a pivot member 116 that is pivotally secured between the frame members 18a and 18b (FIG. 4) of the frame assembly 16 to pivotally secure the bell crank 102 to the frame assembly 16. The clip 90 is formed of a resilient material such that the bell crank pin 104 will deform the clip 90 and exit the recess 90a when the alignment pin pusher 72 is manually advanced by advancing the knobs 58 along the housing 52.

In use, when the clamp slide members 30 are advanced, walls of the clamp slide members 30 defining the cam slots 112 engage the cam members 110 (FIG. 8) to pivot the bell crank 102 about the pivot members 116 in relation to the clamp slide members 30. When bell crank 102 pivots with the bell crank pin 104 in an active position received within the clip 90, the bell crank pin 104 advances the alignment pin pusher 72 distally in relation to the clamp slide members 30 to advance the distal abutment member 76 (FIG. 6) within the slot 78 (FIG. 7) of the cartridge assembly 24 to advance the alignment pin 80 from a distal end of the slot 78 of the cartridge assembly 24 into engagement with anvil 22 (FIG. 12). The cams slots 112 are configured to pivot bell crank 102 during the initial advancement of clamp slide members 30 to quickly advance alignment pin pusher 72 and the alignment pin 80 of the cartridge assembly 24 into the anvil 22 during the initial stage of approximation of the stapling device 10. Advancement of the alignment pin 80 into engagement with the anvil 22 maintains alignment between the anvil 22 and cartridge assembly 24 during approximation of the tool assembly 14 and also retains tissue within the tool assembly 14.

Referring briefly to FIGS. 1, 2, and 9 the bell crank pin 104 extends through an elongated, curved slot 120 (FIG. 2) defined in the housing 52 and includes a grip member 122. The slot 120 is configured to accommodate pivotal movement of the bell crank pin 104 as the bell crank 102 pivots about the pivot member 116 (FIG. 9) in response to translation of the clamp slide members 30 within the frame assembly 16. The grip member 112 is positioned externally of the housing 52 and can be grasped by a clinician to move the bell crank pin 104 transversely from an activated position to an inactivated position. In the activated position (FIGS. 10 and 11), the bell crank pin 104 is received within the openings 114 of the side walls 108 of the bell crank 102 and within the clip 90 of the alignment pin pusher 72. With the bell crank 102 coupled to the alignment pin pusher 72, longitudinal movement of the clamp slide members 30 causes pivotal movement of the bell crank 102 to cause longitudinal movement of the alignment pin pusher 72. In the deactivated position of the bell crank pin 104, the bell crank pin 104 is withdrawn from the openings 114 in the side walls 108 of the bell crank 102 and from the clip 90 of the alignment pin pusher 72 such that the bell crank 102 is no longer coupled to the alignment pin pusher 72. When the bell crank 102 is not coupled to the alignment pin pusher 72, pivotal movement of the bell crank 102 is not translated into movement of the alignment pin pusher 72 and, thus does not cause advancement of the alignment pin 80 of the cartridge assembly 24.

Referring to FIGS. 8-12, when the trigger 54 (FIG. 1) is moved towards the stationary handle 52a of the housing 52, the clamp slide members 30 are advanced by a bi-linkage assembly (not shown) such that the cam slots 112 (FIG. 11) of the clamp slide members 30 move in relation to the cam members 110 of the bell crank 102. Movement of the cam slots 112 in relation to the cam members 110 causes the bell crank 102 to pivot in the direction indicated by arrow "A" in FIG. 11. When the bell crank assembly 100 is in the activated position with the bell crank pin 104 positioned within the recess 90a of the clip 90 of the alignment pin pusher 72, pivotal movement of the bell crank 102 will be translated to the alignment pin pusher 72 by the bell crank pin 104 such that the alignment pin pusher 72 and the alignment pin 80 will be automatically advanced in the direction indicated by arrows "B" in FIG. 12 to move the alignment pin 80 into engagement with the anvil 22 (FIG. 12). In the advanced position of the alignment pin pusher 72, the alignment pin 80 captures tissue "T" (FIG. 12) between the anvil 22, the cartridge assembly 24, and the alignment pin 80.

Figure 14:
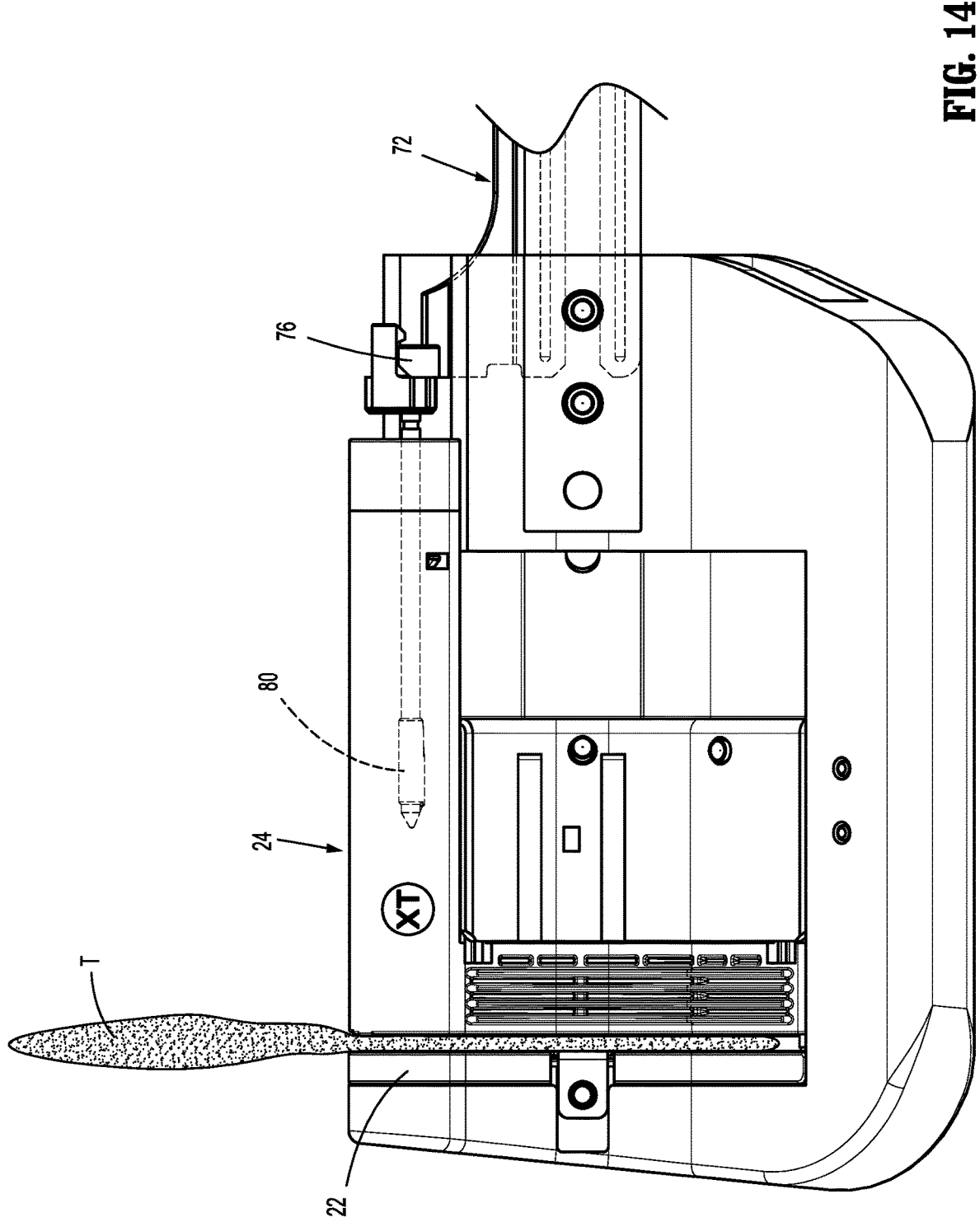
FIG. 14 is a side view of the distal portion of the stapling device of FIG. 12 with the tool assembly in the clamped position and the alignment pin assembly in the retracted position.

Referring to FIGS. 13 and 14, when the bell crank assembly 100 is moved to the inactivated position (FIG. 13) and the clamp slide members 30 are advanced, the rotation of the bell crank 102 does not cause movement of the alignment pin pusher 72 because the bell crank pin 104 is withdrawn from the recess 90a of the clip 90. Thus, the bell crank 102 will move independently of the alignment pin pusher 72. The slots 92 (FIG. 13) in the intermediate portion 88 of the alignment pin pusher 72 accommodate movement of the bell crank 102 independently of the alignment pin guide 72.

The stapling device 10 described above allows for manual advancement of the guide pin pusher 72 and guide pin 80 by advancing the knobs 58 along the housing 52. As described above, manual advancement of the guide pin pusher 72 will disengage the bell crank pin 104 from the clip 90. The stapling device 10 also allows for automatic advancement of the guide pin pusher 72 and guide pin 80 in response to approximation of the stapling device 10 via the interaction of the bell crank assembly 100 with the clamp slide members 30 and the clip 90 of the alignment pin pusher 72. In addition to manual and automatic advancement, the stapling device 10 allows for disabling of the alignment pin pusher 72 and alignment pin 80 by deactivating the bell crank assembly 100 by disengaging the bell crank pin 104 from the alignment pin pusher 72.

FIGS. 15-17 illustrate an alternate embodiment of the bell crank of the presently disclosed stapling device. In embodiments, the bell crank 202 includes an upper stabilizing member 206 that extends between the side walls 208 of the bell crank 202. In embodiments, the stabilizing rib 206 defines a portion of the openings 214 that receive the bell crank pin 204. The stabilizing rib 206 may have bend 206a to facilitate passage of the clip 290 of the alignment pin pusher 272 when the alignment pin pusher 272 is advanced manually independently of the bell crank 202. The bell crank 202 functions in a manner substantially similar to bell crank 102 and will not be described in further detail herein.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A stapling device comprising:
   a handle assembly including a housing defining a stationary handle and a trigger, the trigger being pivotably supported on the housing;
   a frame extending distally from the housing;
   a tool assembly supported on the frame, the tool assembly including an anvil and a cartridge assembly, the cartridge assembly including an alignment pin and being movable along the frame assembly between an open position and clamped position;

an alignment pin assembly including an alignment pin pusher, the alignment pin pusher including an abutment positioned to engage the alignment pin in the cartridge assembly, the alignment pin pusher being movable between a retracted position and an advanced position to move the alignment pin from a position within the cartridge assembly to a position extending from the cartridge assembly;

an approximation mechanism supporting the cartridge assembly, the approximation mechanism being coupled to the handle assembly and being movable from a retracted position to an advanced position in response to actuation of the handle assembly to move the cartridge assembly from the open position to the clamped position; and a linkage assembly including a member extending through the housing that is accessible to a clinician, the member being movable from an activated position to a deactivated position, wherein in the activated position, the linkage assembly couples the alignment pin assembly to the approximation mechanism such that movement of the approximation mechanism causes movement of the alignment pin pusher and in the deactivated position the alignment pin assembly is uncoupled from the approximation mechanism, and wherein movement of the member from the activated position to the deactivated position withdraws the member from within the housing.

2. The stapling device of claim 1, wherein the linkage assembly includes a bell crank assembly having a bell crank and the member, the member including a bell crank pin.

3. The stapling device of claim 2, wherein the bell crank pin is pivotably connected to the frame and the bell crank pin, in the activated position, is coupled to the approximation mechanism.

4. The stapling device of claim 3, wherein the approximation mechanism includes clamp slide members, the clamp slide members having a distal head portion configured to receive the cartridge assembly.

5. The stapling device of claim 4, wherein the clamp slide members define a cam slot and the bell crank includes cam members that are received in the cam slots such that longitudinal movement of the clamp slide members causes pivotal movement of the bell crank.

6. The stapling device of claim 5, wherein the alignment pin pusher includes a clip defining a recess, the bell crank pin being positioned within the recess in the activated position to couple the bell crank to the alignment pin pusher such that rotation of the bell crank causes longitudinal movement of the alignment pin pusher.

7. The stapling device of claim 6, wherein the alignment pin pusher includes an intermediate portion that supports the clip, the intermediate portion defining a channel that accommodates the bell crank when the alignment pin is manually advanced independently of the clamp slide members.

8. The stapling device of claim 5, wherein the clip is formed of a resilient material.

9. The stapling device of claim 8, wherein the clip has a C-shaped configuration such that the bell crank pin can be removed from the recess of the clip when the alignment pin pusher is advanced manually independently of the clamp slide members.

10. The stapling device of claim 9, wherein the alignment pin pusher includes radially extending posts that extend through first elongated slots in the housing of the handle assembly, each of the posts supporting a knob, the knobs being movable along the housing to manually advance the alignment pin pusher.

11. The stapling device of claim 2, wherein the bell crank pin include a grip member positioned adjacent an outer surface of the housing, the grip member being movable to move the bell crank pin between the activated and inactivated positions.

12. The stapling device of claim 11, wherein the bell crank defines at least one opening that receives the bell crank pin when the bell crank pin is in the activated position.

13. The stapling device of claim 11, wherein the housing defines a curved slot and the bell crank pin extends through the curved slot as the bell crank pivots within the housing when the bell crank pin is in the activated position.

14. The stapling device of claim 1, wherein the cartridge assembly includes a body defining a slot, the alignment pin being received within the slot and the abutment being movable within the slot to move the alignment pin from a retracted position located within the slot to an advanced position projecting from the slot.

15. The stapling device of claim 1, wherein frame includes an elongate body portion defining a longitudinal axis and a distal body portion supporting the tool assembly.

16. The stapling device of claim 15, wherein the distal body portion of the frame includes a proximal transverse portion, a linear portion, and a distal transverse portion, the distal transverse portion supporting the anvil.

17. The stapling device of claim 16, wherein the distal body portion is U-shaped.

18. The stapling device of claim 1, wherein the stapling device includes a firing bar that is movable in response to actuation of the handle assembly to eject staples from the cartridge assembly.

* * * * *